United States Patent [19]
Baumgartner

[11] Patent Number: 5,370,697
[45] Date of Patent: Dec. 6, 1994

[54] ARTIFICIAL INTERVERTEBRAL DISK MEMBER

[75] Inventor: Walter Baumgartner, Wil, Switzerland

[73] Assignee: SULZER Medizinaltechnik AG, Winterthur, Switzerland

[21] Appl. No.: 19,717

[22] Filed: Feb. 19, 1993

[30] Foreign Application Priority Data

Apr. 21, 1992 [EP] European Pat. Off. ........ 92810288.8

[51] Int. Cl.⁵ .............................................. A61F 2/44
[52] U.S. Cl. ....................................................... 623/17
[58] Field of Search ................. 623/17, 18, 20; 606/61

[56] References Cited

U.S. PATENT DOCUMENTS

| | | | |
|---|---|---|---|
| 4,309,777 | 1/1982 | Patil | 623/17 |
| 4,759,769 | 7/1988 | Hedman et al. | 623/17 |
| 4,946,378 | 8/1990 | Hirayama et al. | 623/17 |
| 4,963,152 | 10/1990 | Hofmann et al. | 623/20 |
| 5,062,850 | 11/1991 | MacMillan et al. | 623/17 |
| 5,071,437 | 12/1991 | Steffee | 623/17 |
| 5,108,442 | 4/1992 | Smith | 623/20 |

FOREIGN PATENT DOCUMENTS

| | | | |
|---|---|---|---|
| 0369603 | 5/1980 | European Pat. Off. | 623/17 |
| 0317972 | 5/1989 | European Pat. Off. | 623/17 |
| 0346129 | 12/1989 | European Pat. Off. | 623/17 |
| 2636227 | 3/1990 | France | 623/17 |
| 2804936 | 8/1979 | Germany | 623/17 |
| 3023353 | 4/1981 | Germany | 623/17 |
| 0895433 | 1/1982 | U.S.S.R. | 623/17 |

*Primary Examiner*—David Isabella
*Attorney, Agent, or Firm*—Townsend and Townsend Khourie and Crew

[57] ABSTRACT

The artificial intervertebral disk member (1) consists of an upper (2) and a lower (3) support, which are attached in the adjacent vertebrae (32, 33), and of an elastic separator (4). The separator is constructed as a separate insert part (5), which can be inserted from outside into the final position (E) and can be fixed there. The upper support (2) is securely connected to the lower support (3) via the elastic separator (4). This produces a "patient-friendly" implant which can be optimally adapted and revised to suit the patients.

18 Claims, 3 Drawing Sheets

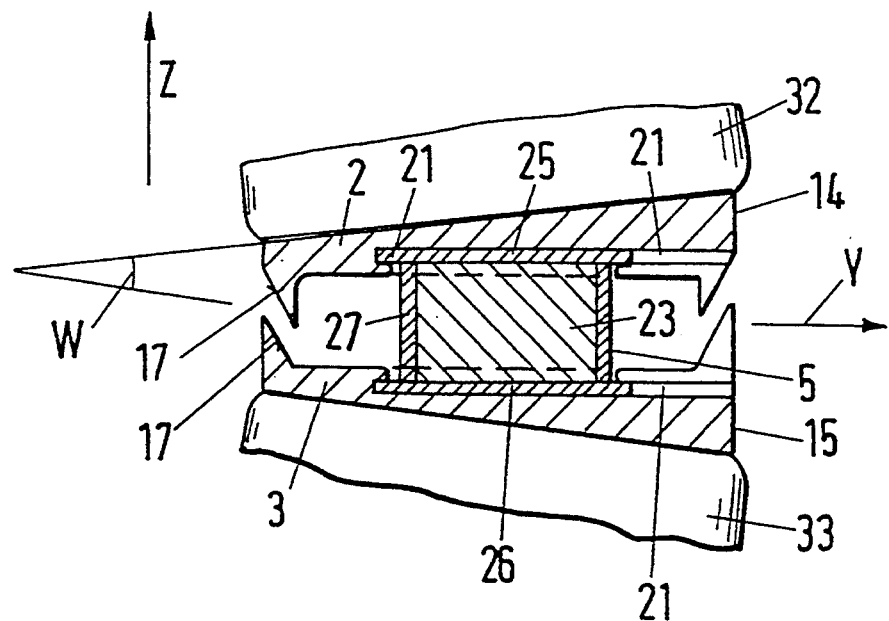
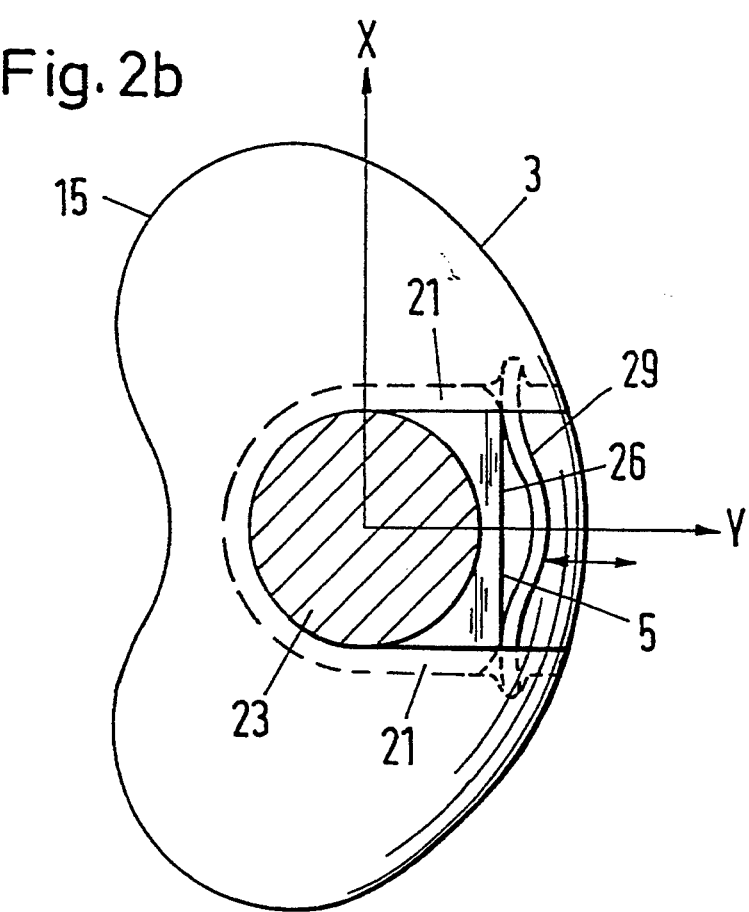

ARTIFICIAL INTERVERTEBRAL DISK MEMBER

BACKGROUND OF THE INVENTION

The invention relates to an artificial intervertebral disk member having an upper and a lower support, which are attached in the adjacent upper or lower vertebra, and having an elastic separator between the upper and lower support. Such intervertebral disk members are known from EP-A-0 317 972, for example. This intervertebral disk member is implanted in the centre of the adjacent vertebral body. So as to maintain the required mobility of the vertebral column and of the vertebral bodies respectively, this intervertebral disk member is by necessity substantially smaller than the cross section of the adjacent vertebral bodies. However, as a result, the loading in the pressure-sensitive centre of the vertebral bodies is so great that they are damaged and that the intervertebral disk member sinks deeper and deeper into the vertebral body as time passes. Thus its function is impaired more and more, and additional damage can occur. A further important disadvantage is that this known intervertebral disk member can not successfully be adapted to the special characteristics of the patient such as weight, condition of the bone substance and position of the intervertebral disk to be replaced in the spinal column. Thus, this artificial intervertebral disk member does not fit very well even at the beginning of the implantation and becomes even worse over time.

SUMMARY OF THE INVENTION

The object of the present invention is, therefore, to overcome these known disadvantages and to create an intervertebral disk member which does not cause any damage to the vertebral body, which can be adapted as well as possible to the anatomical characteristics of the patient so that the mobility of the vertebral column at this place is reproduced and maintained for a long time.

This object is achieved according to the invention with an artificial intervertebral disk member, having an elastic separator constructed as a separate insert part, the elastic separator can be inserted from outside into the final position and can be attached there, making it possible to select and adapt this insert part precisely to the given situation with respect to dimensioning and elastic properties. It would even be possible to try out different exchangeable insert parts intraoperatively. The secure connection of the upper support with the lower support via the elastic separator also prevents in the long term any detrimental displacement of the intervertebral disk member between the adjacent vertebrae.

The separator may comprise an elastic plastic, which is simple and favorable to manufacture. For the purpose of a balanced low load on the vertebral bodies, the support surface may be adapted to the shape of surface of the adjacent vertebral body, and the supports may be constructed as shells which substantially correspond to the cross section of the adjacent vertebral bodies. These shells may have a reinforced edge part and the edge part may form a stop which limits movement. This produces especially favorable load transfers adapted to the adjacent vertebrae. Very favorable properties may also be achieved with a stop, which is constructed both in the vertical direction and also in the directions orthogonal thereto. In a particularly simple and safe embodiment, the insert part is positively connected to the upper and lower support, e.g. by means of a profile for insertion into the supports.

An insert part which is easy to manufacture may comprise an elastomer support member which is securely connected to an upper and a lower rigid cover plate, with it being possible to connect the support members to the cover plates in a positive manner. Suitable cover plates may be made from a titanium alloy or a rigid plastic with fibre reinforcement. Suitable support members may be made from injected or cast elastomer, for example from polyurethane. A further improvement in the elastic properties may be produced by a single-layer or multi-layer reinforcement band around the support member.

A snap fastener produces a particularly simple attachment of the insert part in its final position. The insert part can be adapted to the patient just like an exchangeable modular part with selectable height, angle and elastic properties. The elastic properties may advantageously comprise a first soft zone, then a medium zone and finally a third hard zone with respect to deformation. The soft zone can be determined mainly by the elastic support member, the medium zone by a reinforcement band surrounding it and the hard zone by a stop of the support shell edge part. The exchangeable insert part also enables a simple later revision if the anatomical characteristics change over the years. A new insert part with the appropriate adaptations can be inserted into the supports, without the supports, which have fused with the adjacent vertebrae, becoming loose or having to be removed.

The invention is explained in further detail below by means of examples and figures.

BRIEF DESCRIPTION OF THE PREFERRED EMBODIMENT

FIG. 1a, b shows an intervertebral disk member as specified by the invention with a lateral insertion direction in two views;

FIG. 2a, b shows an example with a ventral insertion direction and an attachment piece;

DESCRIPTION OF THE PREFERRED EMBODIMENT

Figure 1A:
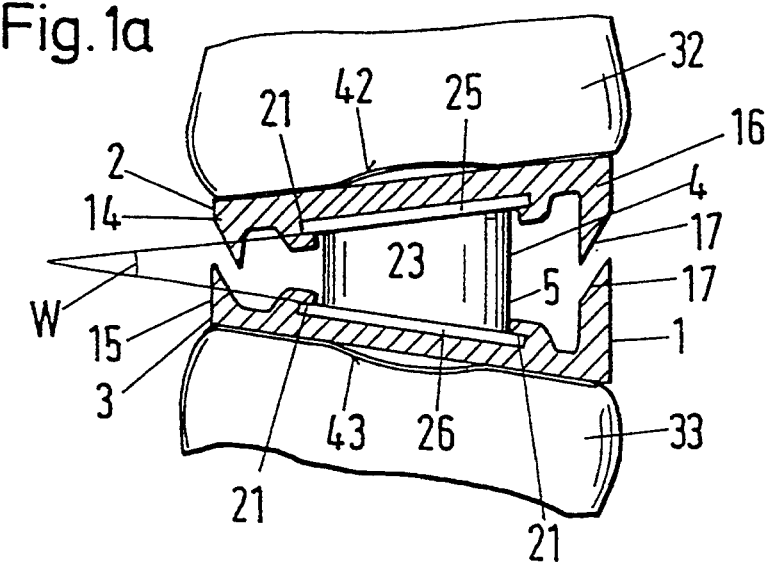
Figure 1B:
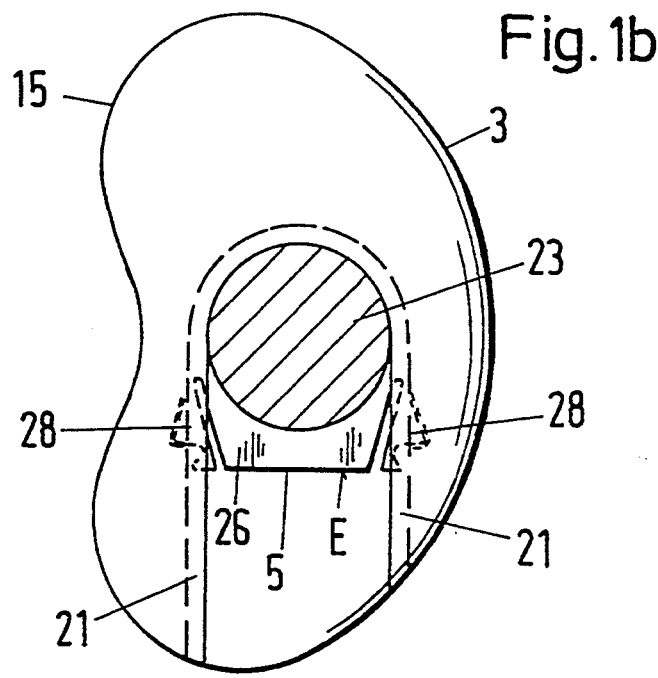
Figure 3:
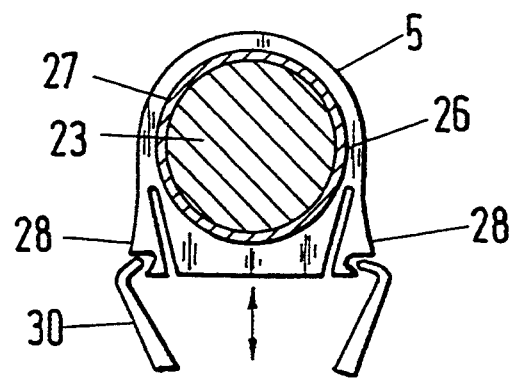
FIG. 3 shows an insert part with snap fastening.

The intervertebral disk member 1, shown in FIG. 1, comprises an upper and a lower support 2, 3, which are tightly connected with the adjacent upper and lower vertebrae 32, 33. An elastic separator 4 is constructed as a separate insert part 5. This can be inserted parallel between the vertebrae 32, 33 from the lateral direction. Here, grooves in the supports 2, 3 and protruding edges of the cover plates 25, 26 of the insert part 5 together form the positive profile 21. In the final position E, i.e. in the centre of the vertebral bodies 32, 33, the insert part 5 is fixed to the supports 2, 3 by a snap fastening 28. The supports 2, 3 are constructed as shells 14, 15, which extend over the entire vertebral cross section and thus produce a good load distribution and transfer. The shells comprise reinforced edge parts 16 which, as stops 17, form a limit or restriction to the relative movement of the supports 2, 3 and thus of the vertebrae 32, 33. In the example of FIG. 1, the intervertebral disk member comprises an angle W of 0° to 20°, for example, corresponding to the curvature of the vertebral column, which is enclosed by the upper and lower support shells 14, 15 and also the cover plates 25, 26. An angle W=0 corresponds to a straight position of the vertebral column. In the example of FIG. 2, the cover plates 25, 26 of the insert part 5 are arranged parallel. The insert part 5 may then be inserted ventrally into the parallel profile guides 21 and be securely and rigidly held in its final position E by a separate retainer spring as fastening spring 29. The support shells 14, 15 also comprise an angle W corresponding to the curvature of the vertebral column. In the example of FIG. 3, the retainer spring 29 and also the snap fastening 28 can be and again detached by special pliers 30 or a clamping tool. Thus the insert part 5 can be exchanged. However other fastenings are also possible, e.g. by a screw connection.

The insert part 5 consists of a central, cylindrical, elastomer support member 23, which is securely connected to cover plates on both sides 25, 26, e.g. chemically or positively by undercut parts. The cover plates may be made from a titanium alloy or fibre-reinforced plastics, for example. The support member is made from elastomer plastic, such as duroplastic or thermoplastic polyurethane, for example, which can be cast or injected in the desired shape between the cover plates 25, 26. A reinforcement band 27 surrounding the support member 23, which is made from single-layer or multilayer PET, for example, is used for the further optimization of the elastic properties of the intervertebral disk member.

Figure 4:
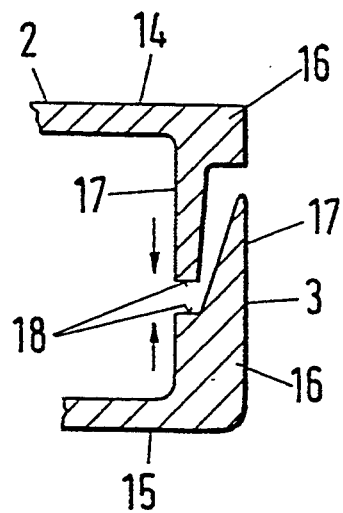
FIG. 4 shows a further stop form of a reinforced shell edge.

A further example of a stop 17 of the reinforced shell edge part 16 is shown by FIG. 4. In the upper part 14, the edge is constructed almost cylindrically and in the lower part 15, it is constructed conically, so that the upper edge is centred on the conical lower edge when pressed together until the two stop planes 18 collide.

Figure 6:
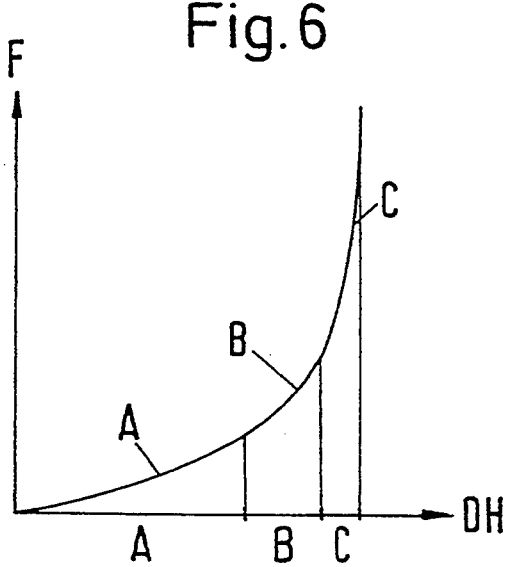
FIG. 6 shows elastic properties with different softness zones.

The elastic properties of such an intervertebral disk member are represented in FIG. 6. The force F occurring as a function of the compression DH of the intervertebral disk member has three different zones A, B, C. The first soft zone A is essentially determined by the shape and hardness of the elastomer support member 23. The following central zone B is in addition essentially determined by the reinforcing band 27 and the hard zone C by the engagement of the shell edge part 16 with stop 17.

The characteristics A, B, C and the dimensioning of the intervertebral disk member with height H, angle W and support shell shape and surface are adapted to each individual patient.

Figure 5:
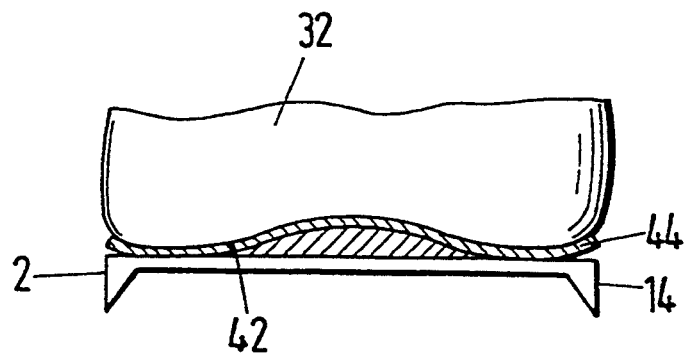
FIG. 5 shows a connection of supports with an adjacent vertebral body.

FIG. 5 shows an attachment of the support 2 with the adjacent vertebra 32. The support shell 2 is provided with a metal lattice 44, e.g. Sulmesh titanium wire lattice, adapted to the vertebral surface 42, into which osseous tissue of the vertebra fuses and thus produces a very good and long-lasting connection with the intervertebral disk member. Thanks to the construction specified by the invention, it is possible to insert a new insert part, which has possibly been modified, into the same fused support shells at a later date if necessary. Thus, changes in the vertebral column caused by age, for example, may also be taken into consideration.

I claim:

1. An intervertebral disk member comprising:
   an upper and a lower support for attachment to adjacent upper or lower vertebrae;
   an elastic separator removably interposable into a final position between the upper and lower supports following their attachment to the adjacent vertebrae and for tightly connecting the upper support to the lower support; and
   a reinforcement band surrounding the elastic separator.

2. An intervertebral disk member comprising:
   an upper and a lower support for attachment to adjacent upper or lower vertebrae;
   an elastic separator constructed as a separate part for insertion into a final position between the upper and lower supports following their attachment to the adjacent vertebrae and for tightly connecting the upper support to the lower support; and
   a snap fastener, operably coupled to the elastic separator, for fixing the elastic separator into the final position.

3. An artificial intervertebral disk member for insertion between adjacent upper and lower vertebrae comprising:
   an upper support attached to the upper vertebra;
   a lower support attached to the lower vertebra;
   an elastic separator removably interposable between the upper and lower supports; and
   the upper and lower supports each having profile guides, the elastic separator being sized to slide within the profile guides into a final position in which the upper and lower supports are tightly connected to the elastic separator.

4. An artificial intervertebral disk member according to claim 3 further including means for securing the elastic separator into the final position.

5. An intervertebral disk member according to claim 3 wherein the upper support has an upper surface that conforms to a lower surface of the upper vertebra and the lower support has a lower support that conforms to an upper surface of the lower vertebra.

6. An intervertebral disk member according to claim 3 wherein the upper and lower supports are constructed as shells which substantially correspond to a cross section of the upper and lower vertebrae.

7. An intervertebral disk member according to claim 6 wherein the shells each comprise a reinforced edge part.

8. An intervertebral disk member according to claim 7 wherein each reinforced edge part forms a stop, the stop being sized and positioned to limit relative movement between the first and second vertebrae.

9. An intervertebral disk member according to claim 8 wherein the stop includes means to limit movement both in a vertical direction and in directions orthogonal to said vertical direction.

10. An intervertebral disk member according to claim 3 wherein the supports each include an undercut portion, the elastic separator being connected positively to the undercut portion of the upper and the lower supports.

11. An intervertebral disk member according to claim 3 wherein the elastic separator comprises an elastomer support member securely connected to an upper and a lower rigid cover plate.

12. An intervertebral disk member according to claim 11 wherein the cover plates each include an undercut portion, the support member being connected in a positive manner with the undercut portions of the cover plates.

13. An intervertebral disk member according to claim 1 wherein the cover plates are made from a titanium alloy.

14. An intervertebral disk member according to claim 11 wherein the support member is made from an injected elastomer.

15. The disk member of claim 4 wherein the securing means comprises a retainer spring.

16. The disk member of claim 15 wherein the upper and lower support profile guides include grooves formed in the upper and lower supports.

17. An artificial intervertebral disk member for insertion between adjacent upper and lower vertebrae comprising:
   an upper support attached to the upper vertebra and having a lower surface, the lower surface having an undercut portion;
   a lower support attached to the lower vertebra and having an upper surface, the upper surface having an undercut portion;
   an elastic separator removably interposable between the upper and lower supports, the separator being sized to fit tightly within the undercut portions of the upper and lower supports to thereby connect the supports.

18. An intervertebral disk member according to claim 1 wherein the elastic separator includes a support member and the supports each include a reinforced edge part, the reinforced edge parts each forming a stop, the stops being sized and positioned to limit relative movement between the first and second vertebrae; and
   the support member, the reinforcement band and the stop each having elastic properties such that the disk member deforms according to three stages, a first soft stage determined by the elastic properties of the support member, a second medium stage determined by the elastic properties of the reinforcement band and a third hard stage determined by the elastic properties of the stop.

* * * * *